(12) United States Patent
Licon et al.

(10) Patent No.: US 7,094,607 B1
(45) Date of Patent: Aug. 22, 2006

(54) APPARATUS FOR HIGH-THROUGHPUT PRODUCTION OF COAT MATERIAL ARRAYS, AND ANALYTICAL METHODS USING SUCH ARRAYS

(75) Inventors: Mark Licon, Diamond Bar, CA (US); Jay R. Akhave, Claremont, CA (US); Dennis L. Saunders, San Dimas, CA (US)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 10/089,807

(22) PCT Filed: Oct. 30, 2000

(86) PCT No.: PCT/US00/29854

§ 371 (c)(1),
(2), (4) Date: Apr. 3, 2002

(87) PCT Pub. No.: WO01/33211

PCT Pub. Date: May 10, 2001

Related U.S. Application Data

(60) Provisional application No. 60/162,349, filed on Oct. 29, 1999.

(51) Int. Cl.
*G01N 31/00* (2006.01)
*C12M 1/34* (2006.01)

(52) U.S. Cl. ............ 436/45; 422/72; 422/102; 422/104; 435/288.2; 435/288.3; 435/288.4; 436/2; 436/85; 436/174; 436/183; 494/10; 494/16; 494/20

(58) Field of Classification Search ........ 436/2, 436/45, 85, 174, 183; 494/10, 16, 20; 422/72, 422/102, 104; 435/288.2, 288.3, 288.4
See application file for complete search history.

(56) References Cited

U.S. PATENT DOCUMENTS

| 4,299,920 A | 11/1981 | Peters |
| 5,985,356 A | 11/1999 | Schultz et al. |

FOREIGN PATENT DOCUMENTS

| CA | 2260807 | 1/1998 |
| EP | 0 363 504 | 4/1990 |

OTHER PUBLICATIONS

Chemical Abstracts, vol. 94, No. 16, Issued Apr. 20, 1961. R.A. Machevakaya et al., "Study of the interrelation of Properties of Coatings and the Composition of Epoxy–Phenol Compositions", see p. 93, col. 1, abstract No. 123179p, Lakokras. Mater. Ikh Primen., 1981, (1), 35–36.

*Primary Examiner*—Arlen Soderquist
(74) *Attorney, Agent, or Firm*—Scott R. Hansen; Fulwider Patton LLP

(57) ABSTRACT

A combinatorial, high-throughput screening method is described for developing new coatings having a performance characteristic of a coating property which results in a substantial increase in the discovery rate of new coating materials. The method includes the steps of providing an array of wells (18) for receiving candidate coating materials having a parameter; placing coating materials in each well (16) while varying the coating material parameter correlating the coating material position in the array to the variation of the coating material parameter; applying a coating leveling force to and optionally drying the coating materials in the array of coating wells (19); testing the coatings with regard to the desired performance characteristic (21) and correlating the result of the test to the well position in the array that thereby coating materials having the desired performance characteristic may be discovered.

18 Claims, 7 Drawing Sheets

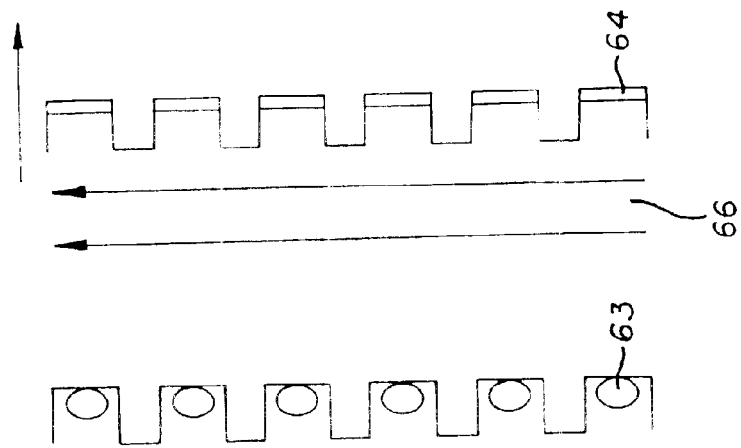
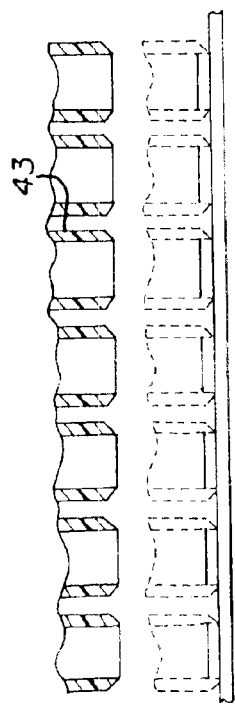
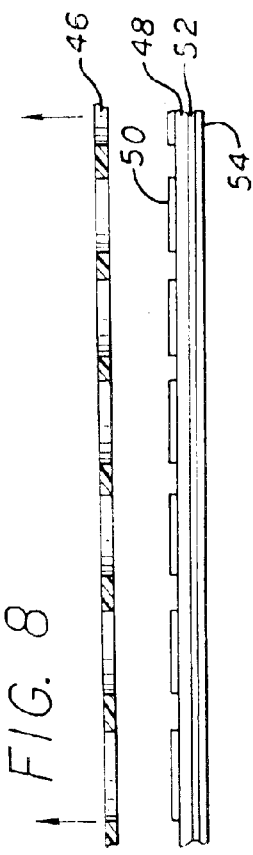

APPARATUS FOR HIGH-THROUGHPUT PRODUCTION OF COAT MATERIAL ARRAYS, AND ANALYTICAL METHODS USING SUCH ARRAYS

RELATED PATENT APPLICATION

This application is a 371 of PCT/4500/29854 filed Oct. 30, 2000, which claims priority from prior U.S. Provisional patent application Ser. No. 60/162,349 filed October 29, 1999, the disclosure of which is hereby incorporated by reference.

BACKGROUND

1. Field of the Invention

The invention relates generally to methods and apparatus for identification and optimization of coating materials and properties for desired applications. More specifically, the invention relates to an improved process of creating coatings, involving identifying candidate materials and screening and optimizing formulations and coating parameters for desired applications.

2. Description of Related Art

Development of coating materials, for example adhesive coatings, release coats, protective coatings, and the like as well as films and laminate constructions of layered materials, has conventionally been a time consuming and labor intensive process. Candidate materials are identified primarily based on knowledge and experience with what compositions have worked before in related applications and investigating like materials and combinations of materials. This usually involves preparing a coating formulation, preparing a test coating for evaluation (often involving several tries to attain the desired parameters such as coat weight, cure. etc. for evaluation), drying the coating, then evaluating the coating by testing the property of interest, such as permeability, tack, shear and bending strength, surface roughness. etc. and entering the results in a database for comparison with further coatings to be developed and tested. Problems of cross-contamination and holdover further limit the number of formulations that can be screened in a given time period. This is a time-consuming process and as a result one skilled in the art, even with support staff to assist and carry on tasks in parallel, has conventionally been able to screen at most a few coatings per day, most often only one or two.

Because of the lengthy time required to screen and then investigate candidate materials and associated coating application parameter values to select and optimize coatings, those skilled in the art generally must focus on families of materials known to possess properties likely to prove successful in the intended use. Investigation of unconventional or simply previously untried materials is usually limited. Moreover, development of coating materials for a particular application is also a time-consuming process, and development of new coatings, while potentially beneficial, sometimes cannot be pursued due to economic considerations arising out of the time and effort involved.

Requisite in the development of new coating materials is the use of a particular coating method as well as consideration of holdover or carryover effects. Holdover effects result in the contamination of one candidate coating material due to residual coating material remaining in the coat dispensing apparatus and/or coal-receiving substrate from a prior test coating material. Contamination as a result of holdover effects are generally additive and provide a level of error in coat formulation that is difficult to control. It is therefore preferable, especially when the volume of coating material to be tested is small, to use a coating method that either eliminates or significantly reduces holdover effects. Use of a disposable method for dispensing as well as receiving the test coat material would eliminate problems associated with holdover effects.

A variety of methods for coating desired substrates or materials are available and include spin coating, die coating and non-contact jet coating methods. Spin coating is a technique commonly used in the field of electronics where the coat material is dispensed onto a desired surface by centrifugal force (spinning). The coatweights resulting from this method are limited to very thin coatings and there is a significant loss of material during the coating process. In both the die coating and non-contact jet coating methods, die and jetting nozzle costs prohibit their modification to disposable units. Prior to the instant application, an inexpensive, efficient and disposable method for testing a large number of coating materials has not been known. While many significant advances in coating technology have been made in recent years, acceleration of the rate at which coating materials can be identified, screened, investigated and optimized will be recognized as a desirable goal by those skilled in the art.

SUMMARY OF THE INVENTION

An object of the invention is to provide a multi-well apparatus for making arrays of coating materials. Such arrays are suitable for analysis and may comprise a disposable two-layer assembly where the first layer contains a plurality of wells and the second layer is a substrate layer. Both layers can be flexible, with the second or bottom layer being detachable from the overlying first layer. Such an apparatus can be made of disposable material, thus providing a cost-effective, efficient and reliable means of making and testing numerous formulations of coating material.

The invention also provides a method of developing a new coating having a desired performance characteristic with regard to a property of a coating, comprising: a) providing an array of coating wells, b) placing a coating material having the known parameter in each coating well, varying the parameter so as to provide a plurality of coatings having different parameter values in a plurality of coating wells; c) correlating the value of the parameter for the coatings deposited in each of the plurality of coating wells with the position of the coating well in the array, whereby a parameter value is associated with each coating well position in the array; d) applying a leveling force to the array of wells to level the coating material in the coating wells; and e) testing the coatings in the array to analyze the relationship between the position in the array and performance with regard to the property of the coating material, whereby the value of the parameter can be correlated to the performance of the coating with regard to the property of the coating. Optionally, the coatings in the array can be dried while the leveling force is applied. The above combinatorial, high-throughput method of screening candidate coat materials results in a significant increase in the discovery rate of new coating materials. In a preferred embodiment the leveling force may be provided by a centrifuge.

Further features, details, and advantages of the invention will be more apparent with reference to the following detailed description, taken in conjunction with the accompanying drawings, which illustrate, by way of example, principles of the invention.

BRIEF DESCRIPTION OF THE DRAWINGS

FIG. 7 is a side view of a flexible well plate having a removable top portion usable in one embodiment of the invention, FIG. 8 is a side view of a well plate having a laminate construction usable in one embodiment of the invention;

FIG. 9 is a schematic diagram showing leveling of coating array materials by application of a leveling force and curing by hot air;

DETAILED DESCRIPTION OF THE PREFERRED EMBODIMENTS

In accordance with one aspect of the invention, it has been recognized that by using automation of certain development processes, miniaturization of samples to be tested, database development and manipulation, and using algorithms to identify candidate materials from information contained in databases, one can increase the number of coating materials that can be developed to meet identified needs. As used herein, the term "combinatorial" refers to the combined approach of high-throughput analysis of libraries consisting of arrays of coat material formulations. Included in the high-throughput analysis are automated or robotic processing of the sample arrays.

Combinatorial methods have been used in the medical, pharmaceutical and biotechnology industries to develop chemical compositions, particularly pharmaceuticals and medicaments, for a number of years. However, these prior combinatorial methods have not been well suited to development of new coatings. Applicants herein provide techniques for generating arrays of coating formulations, well suited to the application of combinatorial chemistry methods. These techniques allow new coatings to be screened and evaluated on a high throughput basis, in order to produce new coatings economically.

Combinatorial Approach

Figure 1:
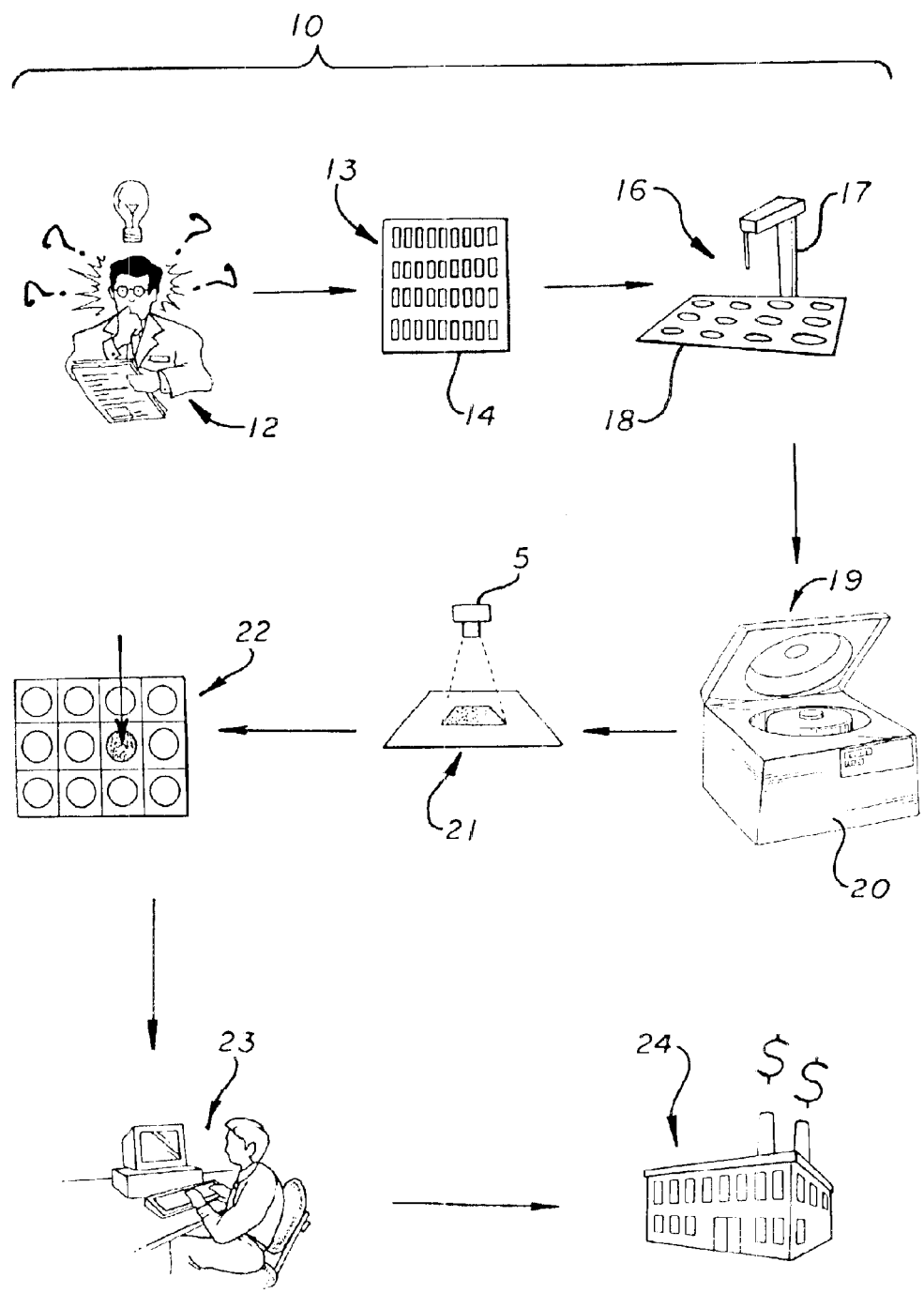
FIG. 1 is a generic schematic of the combinatorial discovery process.

With reference to FIG. 1 of the drawings, which are given by way of example, and not by way of limitation, a system 10 in accordance with principles of the invention comprises a method of developing new coatings by means of a combinatorial approach. A first step 12 is to define what end result coating is desired, and what characteristics and qualities such a coating will have. To achieve the desired result a new material, or a new construction of several materials, such as a laminate for example, comprising new and/or conventional materials combined in a novel way may be required.

At the outset it should be understood that combinatorial methods can be applied to both the process of creating coating materials by formulation or synthesis, and to creating coating parameters or desired characteristics.

Returning to consideration of one example of a combinatorial approach to coating development, the next step 13 is to select likely candidate materials. These can comprise formulations of generally dilute solutions of raw material ingredients 14 that are contemplated as likely elements or components that may provide a coating material with desired characteristics. In the next step 16 a material library of a few to a few hundred thousand, or more, chemical combinations are formed and dispensed into an array of coating wells 18 using a robot or other automated device 17 to make a library or array of coating materials. Incidentally, the "libraries" may include the samples in a single array, or the samples may form a plurality of arrays, processed either concurrently or successively. The chemical combinations forming at least part of the library are then processed in parallel as indicated at reference numeral 19. Processing can include exposing the coating array to a variety of processing variables such as heat, and time as well as applied leveling forces to shape the resultant library or array of coat samples, as can be accomplished, for example, by a centrifuge 20. In the next step 21 high throughput analysis is performed whereby the library is screened by detectors that quickly scan various properties of the coating materials. After the high throughput analysis, materials with the desired properties are identified 22 with the results entered into a large database 23, allowing up to 25.000 variations of materials to be tested at one time. Each library is comprised of one or more arrays of variations of materials to be tested. Each individual site in an array will correspond to a specific formulation of a coat material, wherein the parameter or coat descriptor(s) of the material located at that site is known. Miniaturization of the sample size facilitates processing, and greatly saves cost and time thereby increasing efficiency and the rate of discovery. The end result is discovery and determination of the most successful new material(s) and the process or parameters used to produce the new materials. These materials are then selected for large scale production and commercialization 24.

The combinatorial approach to development and testing of novel coat materials greatly benefits from use of devices and apparatus that allow flat coating samples in the arrays or within wells in the arrays. Additional embodiments encompassing such devices and apparatus are included in the present invention and further described below.

Figure 2:
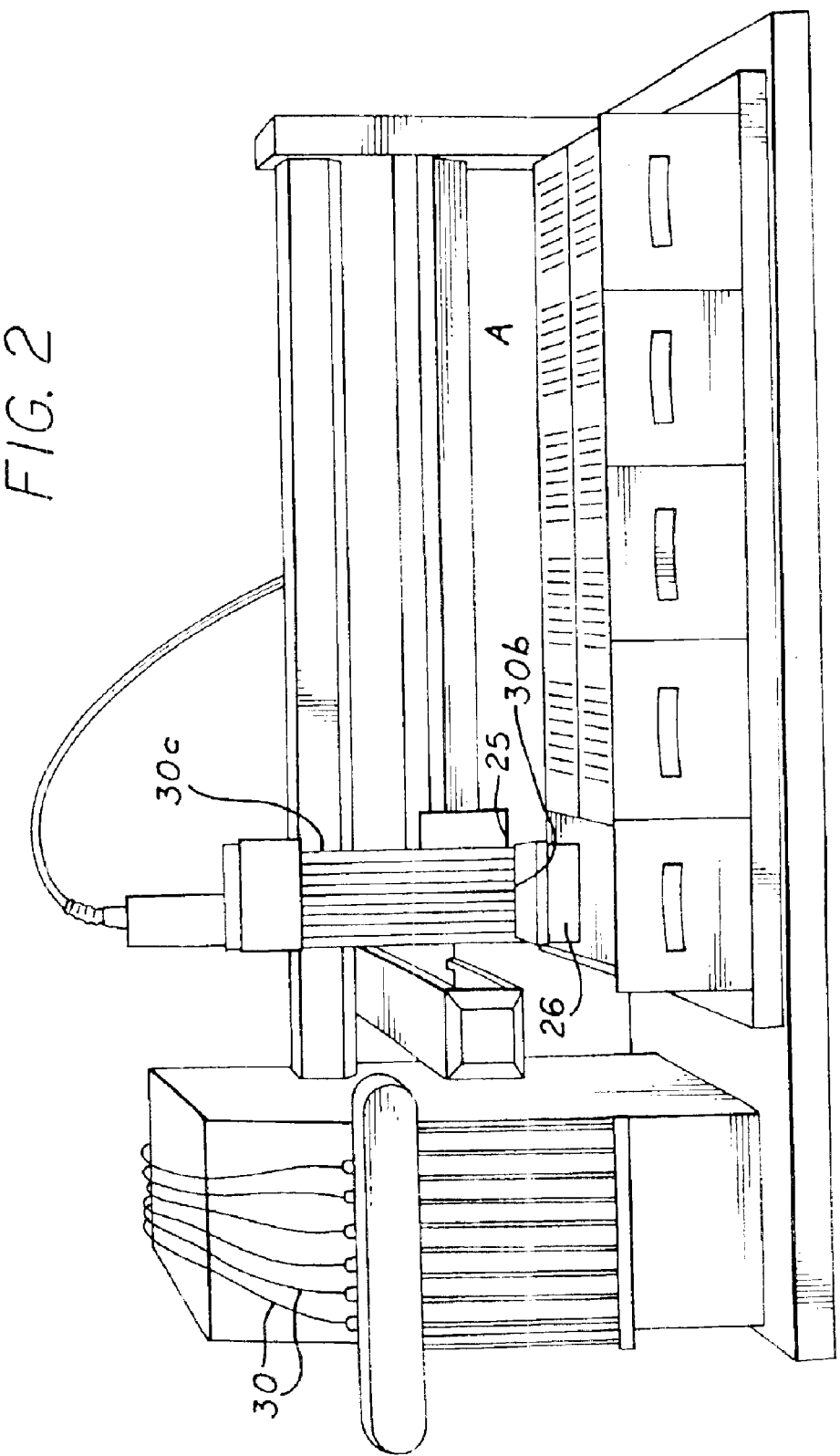
FIG. 2 is a perspective view of an example of a robotic dispenser usable in one embodiment of the invention.
Figure 3:
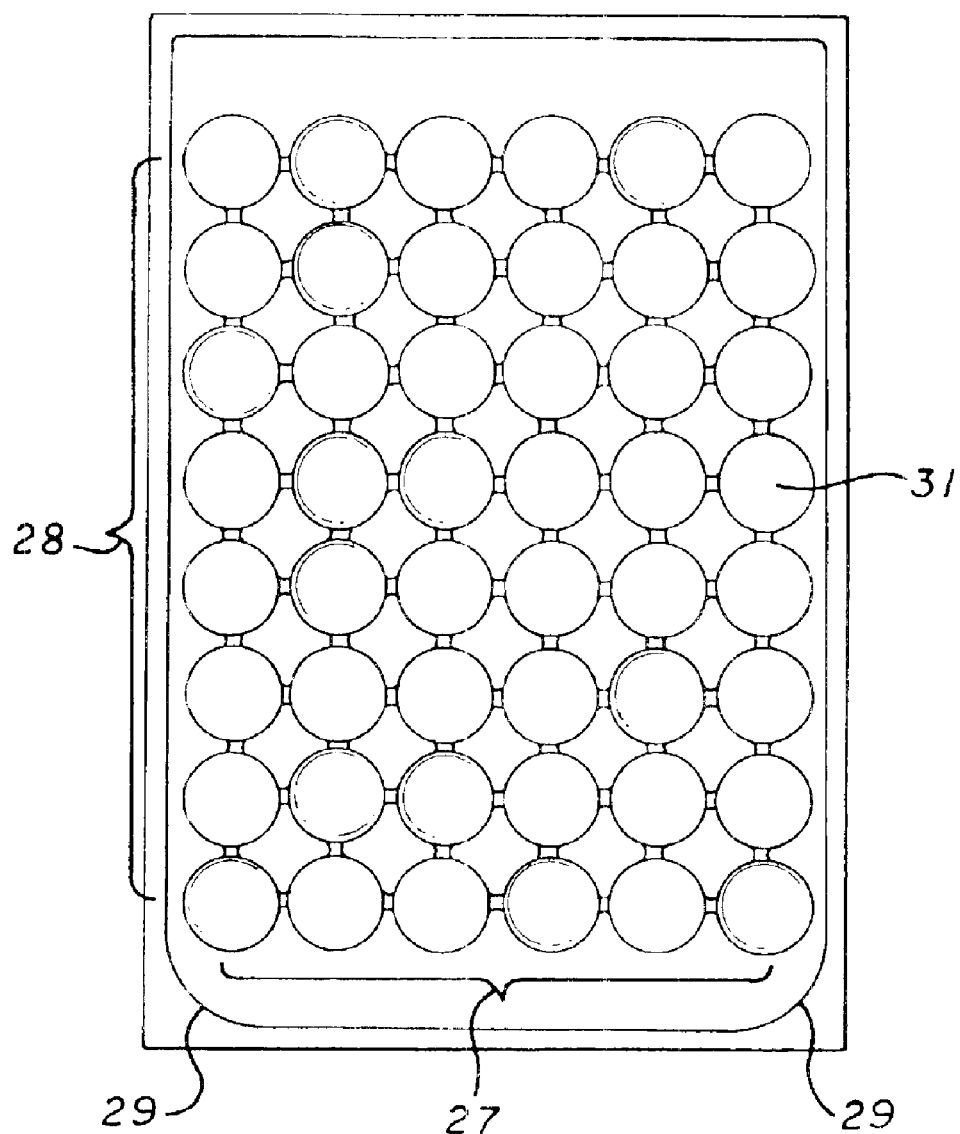
FIG. 3 is a top view of an example of a well plate usable in one embodiment of the invention.

When trying to coat one formulation after another in a rapid fashion, "holdover" considerations are important. As used herein, the term "holdover" is defined as the volume of material that is residual in a cavity after it is emptied and could contaminate the next batch of material deposited into the cavity. As volumes of the cavity get smaller, the potential for holdover increases. For example, tubes, pipette tips, material dispensers and such all have potential holdover volumes. The contamination is also a function of the rheological nature or viscosity of the material that is deposited into the cavity. Holdover effects in traditional methods of developing coating materials greatly increases the level of error, compromising the identification of correct parameters of a new coat material. In the present invention, holdover and its contaminating effects are eliminated by use of a disposable dispensing device 25 (FIG. 2) and a disposable substrate assembly (formatted as a multi-well apparatus) 26, both of which are further described below. As used herein, the term "substrate" is defined as any coat-receiving surface or material, or a substance upon which a sample coat material resides which allows the testing of that sample. A "substrate assembly" is a composite of materials formed into a unit or apparatus for holding a large number of different coating samples in an array format (FIG. 3). An "array format" as used herein, is a matrix format where the samples of coating material are arranged as discrete coated areas 31 on a surface, such as a planar surface. For example, a 48-well coating array (FIG. 3) would have 48 discrete coated areas arranged as 6 rows 27 and 8 columns 28.

Multi-well Apparatus for Parallel of a Material Library

An initial step in the development of a coating is to create the various mixed formulations to be placed in the wells in the array. In one embodiment of the present invention, such sample formulations can be mixed or prepared in a multi-well plate format (FIG. 3) with each individual well containing a unique, pre-defined formulation to be tested. A variety of types of commercially available multi-well plates suitable for use in the present invention can be used (Millipore Corp., Polyfiltronics. VWR Scientific). Such multi-well plates can vary in size of plate dimension, size of well (outer circumference as well as well-depth), type of material used to construct the multi-well plate (for example, polystyrene or polypropylene, rigid plastic or flexible plastic). The biotechnology and pharmaceutical industry utilizes multi-well plates (generally 48-, 96- or 256-well plates) whose outer dimensions are standardized for use with robotic dispensers. Generally, standardized multi-well plates are rectangular, rigid, stackable plates with right edges of the top or lid portion being curved 29. The outside dimensions of a complete multi-well unit are approximately 5×3.25 inches. Such multi-well plates are suitable for use in the present invention. In general, the well size used should be of substantial volume so as to allow adequate robotic mixing of the required or needed amount of each formulation without drying up of the solutions contained in the wells. Preferably a well volume of 0.5 to 3 cubic centimeters in volume is contemplated for use in the present invention. The minimum quantity or volume of sample to be mixed in a "mother" wellplate will vary depending upon the desired coating thickness, domain size and formulation of the coating solution.

As used herein, a "mother" well plate is defined as a source well plate. For example, a 25 micron thick coating that is 1 $cm^2$ in domain size with a coating solution that is 50% solids, will require (1 $cm^2$×25 microns/0.5) volume units or 0.0050 cc of solution. "Domain size" as used herein, refers to the minimum area required for the coated sample as determined by downstream testing. The appropriate volume of individual formulations from this mother well plate can then be dispensed to a sample or "daughter" well plate to make a coating with the desired domain size for subsequent analysis and data collection. It should be understood, that alternative embodiments include use of a single well plate as both the mother and daughter well plate. In such a case, the well plate into which the sample formulations are mixed will also serve as the well plate from which the coating materials will be tested. Again, considerations of desired coating thickness, domain size and formulation of coating solutions will be included in determination of minimum volume of well size required. Additional embodiments of well plate apparatus design will be discussed further below.

Automated Dispensing of Candidate Coat Materials for Testing

A disposable metering device can be used to dispense the formulations from a mother well plate to a daughter well plate. A robotic dispenser (available commercially for example, from Hamilton Zinser Packard) (FIG. 2) is one such device. Robotic dispensers allow for rapid and automated dispensing of a specified quantity of a large number of samples. The well plate format to be used for the daughter well plate will also depend on the domain size requirement of the coating. For example, a 6-, 12-, 24-, 48-, 96-, or 384-well plate format are commercially available formats which can be used in the present invention with the commercially available robotic dispensers. The robotic dispenser will have a platform area upon which the substrate well plates reside (FIG. 2. "A").

Alternatively, in the case where a single well plate is used as both the mother and daughter wellplate, a robotic device can also be used for mixing as well as dispensing component materials for the sample coating formulation to be tested. Such a device could have multiple dispensing units 30 from which specific and precise amount of an individual component is dispensed into a single well. The sample solution can be dispensed using disposable pipette tips 30b attached to the pipettors 30c. For example, a separate dispensing unit for each component can be used to dispense the appropriate amount of a respective component into a single sample well. Such a dispensing unit can be disposable which will allow rapid and accurate automation of the combinatorial method for formulating or synthesizing a new coating with elimination of holdup or contamination problems. Examples of disposable dispensing units include, polyethylene or other type of tubing and disposable pipette tips.

Alternative Designs of Multi-well Apparatus for Parallel Processing

Figure 4:
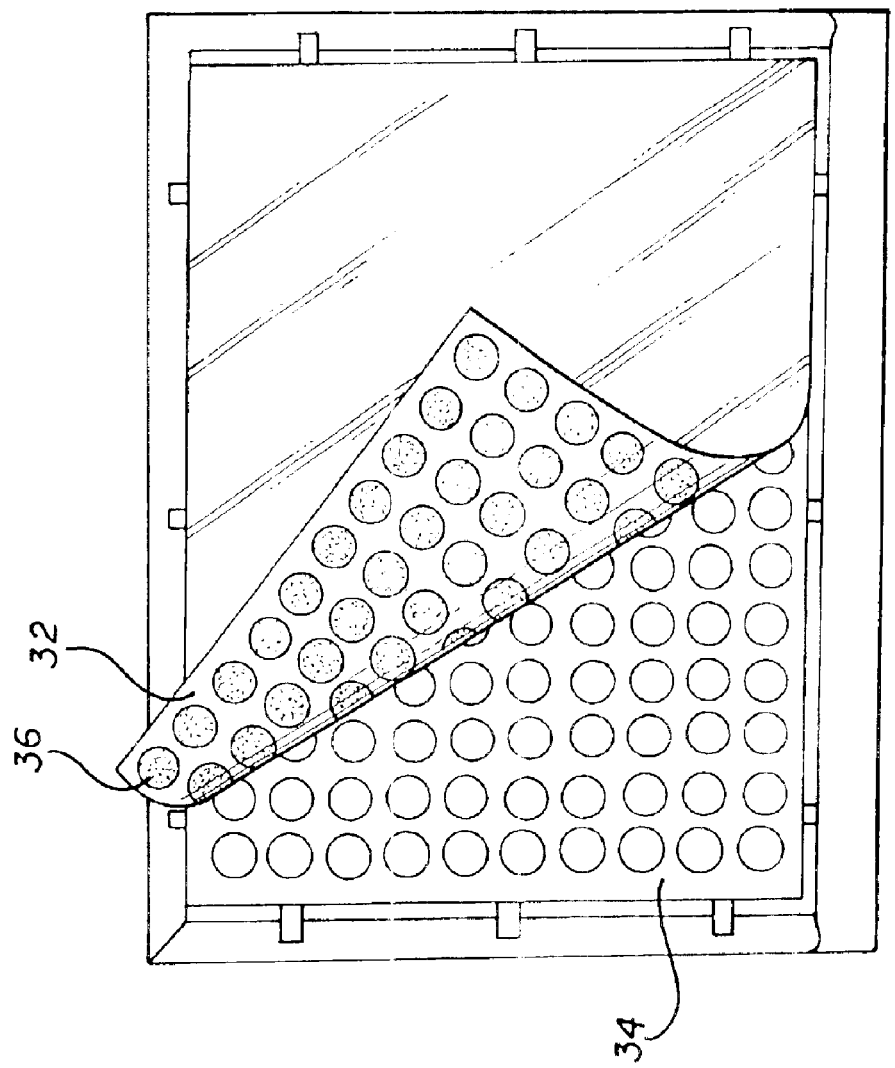
FIG. 4 is a perspective view of an example of a well plate having a removable well bottom, comprising a substrate to which sample coatings are applied, usable in one embodiment of the invention.
Figure 5:
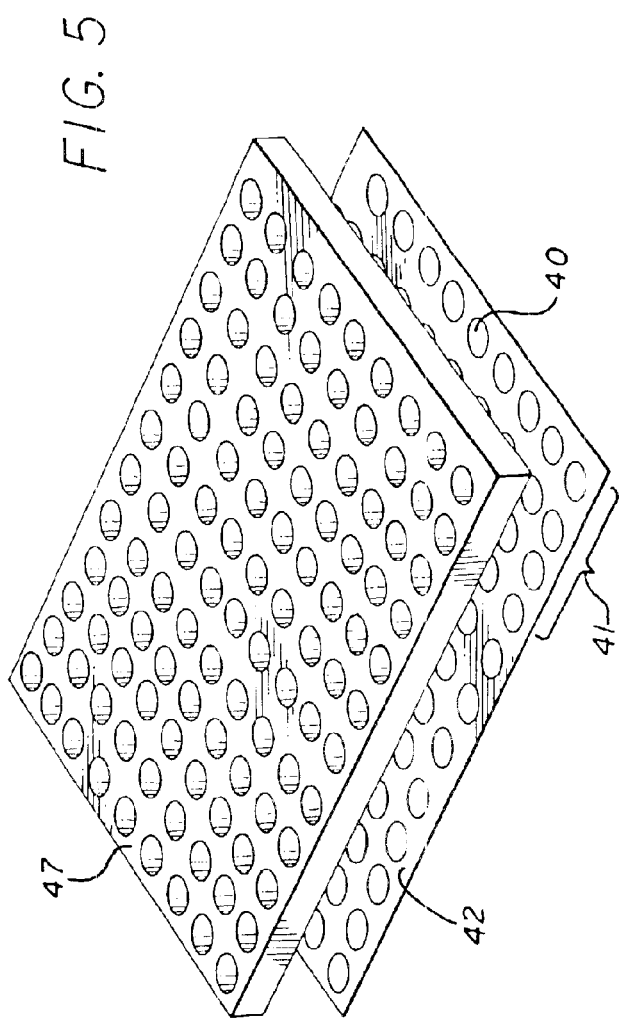
FIG. 5 is a perspective view of another example of a well plate having a removable well bottom comprising a substrate to which sample coatings are applied, usable in one embodiment of the invention.

Alternative embodiments of well plate design include providing a two-piece coating well apparatus having at least a substrate portion 32 and a multi-well or sample-containing template 34 which can be separated from one another (FIG. 4). Once leveled and dried, the coating material 36 is held by the substrate portion 32 of the assembly. This type of well plate assembly is designed such that the base substrate-portion (or bottom half of the assembly) 32 can be removed from the multi-well template portion 34 of the well plate assembly. Various embodiments of a well plate design having a removable bottom are contemplated and further described below. FIG. 5 shows an example of a multi-well plate depicting the array format useful in the invention. Coating material samples are placed within the apertured, multi-well template top 47. Such multi-well plates will form an array 41 or library format of the different formulations as discrete coated areas 40 on a planar substrate sheet 42. A multi-well plate with a removable top or cover can also be used as a well plate assembly. An example of such a multi-well plate design is shown in FIG. 7. The well plate design can also include modifications to the well plate to prevent distribution of coating material onto the inner walls of the wells. For example, a release coating can be applied to the inner walls 43 of the wells to prevent any sample material from moving up and onto the well walls during application of a leveling force.

Figure 6:
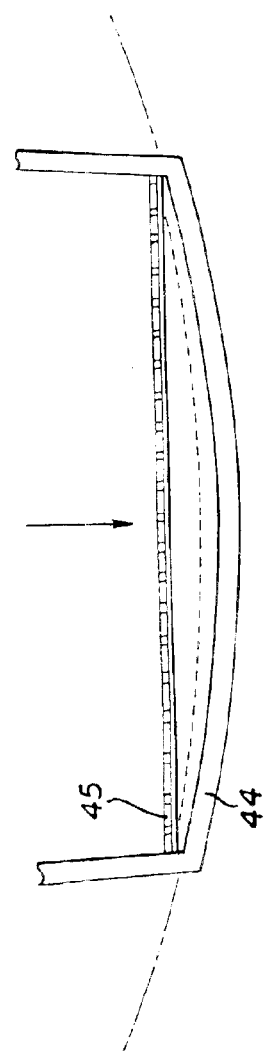
FIG. 6 is a side view of a well plate having a curved bottom usable in one embodiment of the invention.
Figure 10:
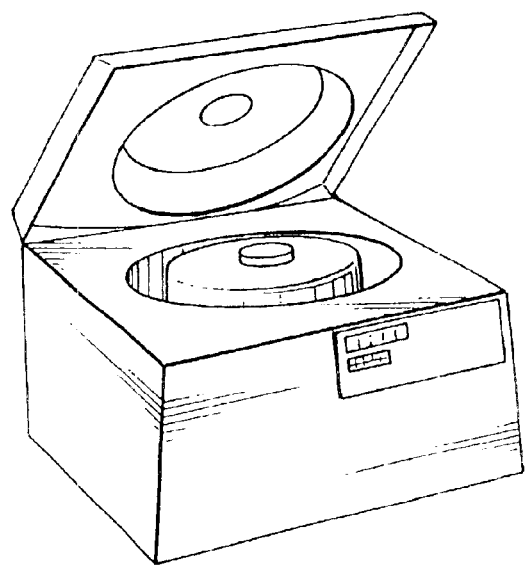
FIG. 10 is a perspective view of an example of a centrifuge usable in an embodiment of the invention.

An additional embodiment of the present invention includes multi-well plates designed to obtain flat coatings in all of the wells of assembly. Current commercially available multi-well plates have a flat-bottom surface for the entire plate. This results in an uneven distribution of sample material in the wells located along the perimeter of the multi-well plate 68 when current swing arm type of centrifuge rotors 70 are used to apply a leveling force. FIG. 6 shows an example of a modified multi-well plate designed to obtain flat coatings in all of the wells. Such a well plate will have a curved base plate 44 where the curvature of this base is parallel to the circumference of the centrifuge rotor, or is curved so as to substantially match the curvature of the curvilinear path of the well plate during centrifugation. With a curved-bottom well plate 44, sample material or coating solutions in all of the wells, including perimeter wells 45, will be at the same distance from the spin axis of the centrifuge. Thus, coating material in all of the wells will have a flat distribution following centrifugation. The top view of such a multi-well plate can be as depicted in FIG. S. A flexible substrate and apertured well plate may be employed to provide a curved configuration when mounted in a centrifuge.

A specialized laminate well plate construction is also envisioned as an alternative embodiments of the present invention. FIG. 8 shows a cross sectional view of a representative laminate multi-well plate assembly. In one case, the assembly is made up of at least 4 layers and is shown in FIG. 8. The top or first layer 46 corresponds to the multi-well or sample holding portion of the assembly. This layer need only be thick enough to provide a sufficient barrier between adjacent wells so that the dispensed coating material 50 does not cross contaminate adjacent samples. Where a very small amount of coating material 50 is to be tested, this layer need not be very thick and could be made of, for example, thin plastic, foam or paper with each well formed of holes placed in linear, multiple rows to form an array pattern. Preferably, the top layer will be about 0.01 to about 1 mm, or about 1 to about 10 mm, or about 1 to about 5 cm in height. This top layer 46 can be coated with a Pressure Sensitive Adhesive (PSA) (not shown) to attach it to the substrate layer 48. This will also help to seal the wells so that cross-contamination of sample coating material from one well does not mix with its neighbors. The second layer is the substrate layer 48 and can be formed of a variety of materials, such as plastic, polymeric resin or paper, so long as it will hold the sample coating material 50 in a flattened manner. The second layer will preferably be about 1 to about 100 microns, or about 1 to about 10 mm, or about 1 to about 5 cm in thickness. The third layer is a Pressure Sensitive Adhesive layer (PSA) 52. The PSA layer 52 can be about 5 to about 30 μm, or about 0.005 to about 0.03 mm, or about 0.0005 to about 0.003 cm in thickness depending upon the type of adhesive and degree of adhesion desired. The fourth layer is a liner 54 coated with a release layer such as silicone, which can be removed or peeled away from the PSA layer 52 leaving the adhesive on the bottom of the substrate layer as the new bottom layer. This type of multi-well plate design is suitable for example, where the stickiness or tackiness of a coating material is to be tested. In such a case, it is desirable to have an array library which will remain stationary or adhere to a support surface by the PSA layer 52 while each individual coating sample is tested. Use of the PSA 52 on the layer 48 will allow the array library to remain stationary and not lift up during testing.

Leveling Force

Once the different formulations are dispensed into a multi-well plate assembly 63, the coat formulations are made into flat coatings 64 within the wells by use of a leveling force. A "leveling force" as used herein, is defined as any force sufficient to cause a sample or coat material to distribute evenly and flatly onto a substrate. A leveling force will also remove any residual air bubbles present within the sample coat formulation. A variety of leveling forces are contemplated for use in the present invention including, for example, use of centrifugal force, use of a vacuum or negative pressure force, use of an electrostatic force, or use of a magnetic force. In the case where magnetic leveling force is used, the test coat formulation will contain magnetic force, powder, or a compound such as ferrite, that is responsive to a magnetic force. Use of a leveling force need not be limited to single-coat assessments. Where the processing of a multi-layer construction of coat material is desired, a leveling force can be repeatedly applied following dispensing of individual layers of a coat to be tested. The final array obtained will be a planar sheet containing discrete areas in a grid format of multi-layer coat formulations.

Figure 11:
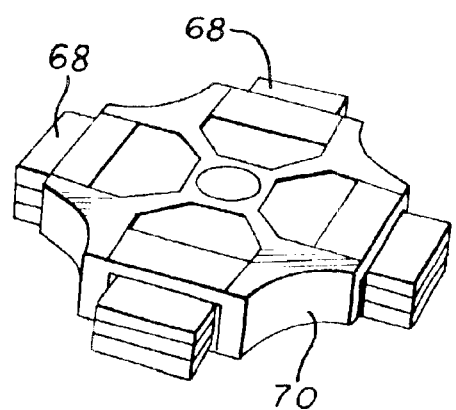
FIG. 11 is a perspective view of an example of a swing arm centrifuge rotor assembly usable in one embodiment of the invention, showing the assembly loaded with well plates.
Figure 12:
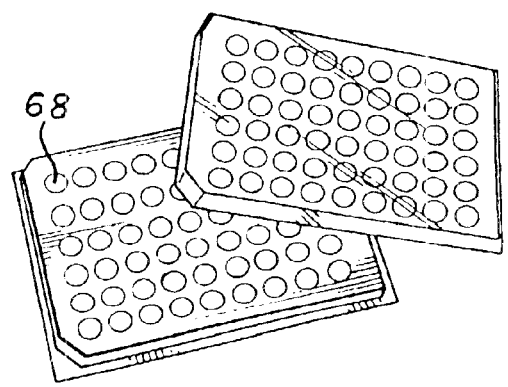
FIG. 12 is a perspective view of an example of a 96-well plate usable in one embodiment of the invention.

FIG. 11 shows an example of a centrifuge that can be used for applying a leveling force to a multi-well plate. Such swing arm-type centrifuges with multi-well plate holders (FIG. 12) are available commercially (for example, VWR Scientific. "MicroPlus GH 3.8 rotor centrifuge"). The rotor for use in such a centrifuge is designed so as to hold an even number of multi-well plate assemblies. The multi-well plate assemblies 68 are loaded into the rotor 70 in an upright or horizontal position. During centrifugation, the plates are directed into a vertical position which then levels or flattens the sample formulations onto the substrate layer. After the formulations are dispensed in a multi-well plate assembly, the assembly is placed in a swing-arm centrifuge and the coatings are spun at controlled speeds so as to form a flat coating within each well 64. For example, with a standard centrifuge, a 10-min, spin at 2000 rpm will be sufficient to evenly distribute the coat materials within each well. There is no loss of sample material with use of a swing-arm centrifuge.

Additional methods of casting sample coat formulations include those which can also simultaneously dry the coating material during casting. For example, a centrifuge which has been modified to hold circulating hot air or other gas which will aid in the evaporation of carrier solvents in the coating formulations is also contemplated for use in the present invention and is diagrammed schematically in FIG. 9. The hot air 66 circulating over the formulations during centrifugation aids in the drying of the coating by evaporation of volatiles or solvents. As with a centrifuge, devices used to provide alternative methods of applying a leveling force can also be modified so as to simultaneously dry the coat formulations. For example, an apparatus utilizing a vacuum or electrostatic force as the leveling force can be modified to circulate hot air and include alternate arrangements for drying.

High Throughput Analysis, Data Storage, Data Modeling and New Materials Discovery The above methods provide an array 40 of coating materials with each site in the grid array containing a coat material having a known parameter which differs from parameter values of the materials contained on the other sites (FIG 1; step 16). With this array, the plurality of coating materials can each be tested for performance of each coating. Because the parameter value of the coating contained at each site is known, the value of a parameter associated with a desired performance of a coating can be determined. All information obtained by this high throughput analysis screening a coat material library are then entered into a database. From this database identification of the most successful new coat materials and the parameters and descriptors used to produce them is achieved (FIG. 1. step 23). Such a database will also serve as a storage library to aid in the formulation of future parameters to characterize the coatings.

EXAMPLE I

This example demonstrates the use of a multi-well plate combined with a centrifugal leveling force for estimation of coat weight of a sample coat material formulation. This example is intended to be representative of one embodiment of the invention, and not intended as limiting the scope of the invention.

The emulsion polymer formulation used was S-2000. S-2000 is a nondispersable emulsion acrylic polymer manufactured by Avery Dennison Corporation. Pasadena Calif. in accordance with U.S. Pat. No. 5,221,706. A 96-well plate obtained from Polytronics was used as a daughter well plate. The well plate remained flat during centrifugation. Each well contained an equivalent sample material formulation for determination of coat weight.

Diameter of each well=0.6 cm
Cross-section of each well=3.14×0.6 cm2=1.884 cm2
Weight of coat material in E7 position of array=0.0153 gm
Wet coat weight in E7=0.0153/0.0001884=81.21 gsm
% solids in wet solution=52.1%
Dry coat weight in E7=42.3 gsm.
Results:

The emulsion did not dry fast and remained opaque. Hence the need for higher temperature drying. Material in wells located on the perimeter wells did not level evenly. Coat material dispensed into the center wells were centered and evenly flattened in the horizontal direction. The uneven leveling observed in the perimeter wells is believed to be a result of the centrifugal force acting at an angle to the bottom of the well, unlike the preferred flexible configuration of FIG. 6.

This example demonstrates the utility of using a multi-well plate combined with a leveling force for high-throughput analysis of specific parameters or characteristics of coat material formulations in an individualized manner.

The invention has been described with reference to various specific and preferred embodiments and techniques. However, it should be understood that many variations and modifications may be made while remaining within the spirit and scope of the invention.

What is claimed is:

1. A method for efficiently preparing a large number of sample coatings comprising the steps of:
   (a) forming a series of sample receptacles or wells by providing a flexible substrate and an overlying apertured sheet with the apertured sheet in tight sealing engagement with the substrate;
   (b) applying different samples of material in liquid form into said receptacles;
   (c) placing said flexible substrates with said sample receptacles thereon in a centrifuge;
   (d) activating said centrifuge with said receptacle mounted therein to flatten out the sample material in said receptacles, with the centrifugal force acting perpendicular to the bottom of the receptacles;
   (e) drying said samples while they are within the centrifuge; and
   (f) removing the apertured plate to leave the samples exposed on said substrate.

2. A method as defined in claim 1 wherein said applying step involves the application of various adhesive compositions into said receptacles or wells.

3. A method as defined in claim 1 wherein multilayer samples are formed by repeating steps (b) through (e) prior to step (f).

4. A method as defined in claim 1 wherein an array of at least four wells are formed.

5. A method as defined in claim 1 wherein hot air is applied to the samples during centrifugation.

6. A method as defined in claim 1 wherein said substrate is formed of paper.

7. A method of forming a test coating comprising the steps of:
   forming a receptacle for receiving a material sample, said receptacle having a flat bottom and enclosing sides;
   depositing a fluid material sample in said receptacle;
   mounting said receptacle in a centrifuge with the outward centrifugal force being perpendicular to the bottom of said receptacle;
   activating said centrifuge to flatten the material in the receptacle; and
   drying said material while the sample is being rotated and flattened by the centrifugal action.

8. A method for efficiently preparing a large number of sample castings comprising the steps of:
   forming a series of sample receptacles by providing a substrate and an overlying apertured sheet with the apertured sheet in right sealing engagement with the substrate;
   applying different samples of material in liquid form into said receptacles;
   drying said samples; and
   removing said apertured sheet to leave said material samples on said substrate.

9. A method as defined in claim 8 including the step of applying force to said samples perpendicular to the bottom of said receptacles to flatten out said samples.

10. A method of testing coating materials, comprising the steps of:
    providing an array of coating wells, each well being configured for receiving a coating material having a known composition;
    placing a coating material having a known composition in each coating well, varying the composition so as to provide a plurality of coating materials having different compositions in a plurality of coating wells;
    correlating the composition of the coatings deposited in each of the plurality of coating wells with the position of the coating well in the array, whereby a specific composition is associated with each coating well position in the array;
    placing said coating wells with said compositions into a centrifuge, and activating said centrifuge;
    drying said coating materials; and
    testing the resultant coatings.

11. The method of claim 10 including providing wells in the form of a flexible substitute and a flexible overlying apertured sheet.

12. The method of claim 10, further comprising the steps of:
    curving the said array of coating wells to substantially match the curvature of the curvilinear path of the array during centrifuging.

13. The method of claim 10 including the step of heating of the coating materials while said centrifuge is activated.

14. A method of analyzing coating materials for performance of the coating with regard to a property of a coating, comprising:

providing an array of coating wells, each well being configured for receiving a coating material having a known parameter; said array of coating wells comprising a substrate and an overlying apertured sheet;

placing a coating material having the known parameter in each coating well, varying the parameter so as to provide a plurality of coating materials having different parameter values in a plurality of coating wells;

correlating the value of the parameter for the coatings deposited in each of the plurality of coating wells with the position of the coating well in the array, whereby a parameter value is associated with each coating well position in the array;

drying said coating samples; and testing the coatings in the array to analyze the relationship between the position in the array and performance with regard to the property of the coating material;

whereby the value of the parameter can be correlated to the performance of the coating with regard to the property of the coating.

15. The method of claim 14, further comprising the steps of:

providing a coating well apparatus having at least a substrate part and a well wall part which can be separated;

separating the well wall part from the substrate part after drying, whereby the coating material array is carried by the substrate alone after separation.

16. The method of claim 14, wherein the well depth and volume is substantially greater than that of the coating volume.

17. A method of analyzing coating materials for performance of the coating with regard to a property of a coating, comprising:

providing an array of coating wells, each well being configured for receiving a coating material having a known parameter;

placing a coating material having the known parameter in each coating well, varying the parameter so as to provide a plurality of coating materials having different parameter values in a plurality of coating wells;

correlating the value of the parameter for the coatings deposited in each of the plurality of coating wells with the position of the coating well in the array, whereby a parameter value is associated with each coating well position in the array;

applying a centrifugal force to the array of coating wells to level the coating material in the coating wells;

curing said coating samples under said coating leveling force; and testing the coatings in the array to analyze the relationship between the position in the array and performance with regard to the property of the coating material;

whereby the value of the parameter can be correlated to the performance of the coating with regard to the property of the coating.

18. The method of claim 17, further comprising the steps of:

providing a coating well apparatus having at least a substrate part and a well wall part which can be separated;

separating the well wall part from the substrate part after application of the leveling force, whereby the coating material array is carried by the substrate alone after separation.

* * * * *